United States Patent [19]

Grave et al.

[11] 4,085,255

[45] Apr. 18, 1978

[54] WATER SEPARATION CELL FOR REMOVING THE REACTION WATER FROM THE ELECTROLYTE OF FUEL CELLS AND FUEL CELL BATTERIES

[75] Inventors: Burghard Grave, Erlangen; Heinrich Gutbier, Rottenbach; Michael Deinzer, Nuremberg, all of Germany

[73] Assignee: Siemens Aktiengesellschaft, Munich, Germany

[21] Appl. No.: 770,631

[22] Filed: Feb. 22, 1977

[30] Foreign Application Priority Data

Mar. 12, 1976 Germany ............................ 2610427

[51] Int. Cl.² .............................................. H01M 8/08
[52] U.S. Cl. ........................................ 429/26; 429/34
[58] Field of Search ................................ 429/26, 34

[56] References Cited

U.S. PATENT DOCUMENTS 3,783,107  1/1974  Kohlmuller .......................... 429/12

*Primary Examiner*—John H. Mack
*Assistant Examiner*—H. A. Feeley
*Attorney, Agent, or Firm*—Kenyon & Kenyon, Reilly, Carr & Chapin

[57] ABSTRACT

A water separation cell for removing the reaction water from the electrolyte of fuel cells and fuel cell batteries which comprise a liquid chamber bounded on at least one side by a porous diaphragm, and a gas chamber bounded by the diaphragm and a condensation surface adapted for cooling, in which the liquid chamber is subdivided into two chambers of different size which are arranged on top of each other with the upper, larger chamber serving as the electrolyte space and the lower, smaller chamber taking up the condensate which passes through the porous diaphragm into this chamber due to the pressure of a gas present in the gas chamber.

9 Claims, 2 Drawing Figures

WATER SEPARATION CELL FOR REMOVING THE REACTION WATER FROM THE ELECTROLYTE OF FUEL CELLS AND FUEL CELL BATTERIES

BACKGROUND OF THE INVENTION

This invention relates to water separation cells for removing the reaction water from the electrolyte of fuel cells and fuel cell batteries in general and more particularly to an improved cell of the type having a liquid chamber bounded on at least one side by a porous diaphragm and a gas chamber bounded by the diaphragm and a condensation surface adapted for cooling.

A method for separating the reaction water from the electrolyte of fuel cells or fuel cell batteries in which electrolyte conducted in a closed circuit is led through a water separation cell and is there brought into contact with one side of a diaphragm, and the water vapor is transported through the diaphragm into a gas chamber adjacent to the former is already known. The hydrostatic pressure of the electrolyte in the porous diaphragm is compensated either by the pressure of a gas present in the gas chamber or by the capillary depression pressure prevailing in the diaphragm, and the water vapor is condensed at a cooled condensation surface which forms a boundary surface of the gas chamber opposite the diaphragm. Apparatus for implementing the method comprises a water separation cell which is arranged in an electrolyte loop outside the fuel cell battery and contains a liquid chamber through which the electrolytic liquid flows. The liquid chamber is bounded, at least in part, by the diaphragm, which forms the one wall of the gas chamber which is bounded on the other side by the condensation surface (German Pat. No. 1,671,879 or British patent Specification No. 1,208,671).

The separation of the reaction water according to this diffusion-condensation principle has proven itself in practical use. The water separation cell or the gas chamber bounded by a nonporous condensation surface is in general connected to a lock for the continuous automatic removal of the condensed water, i.e., the condensed reaction water. A porous disk is arranged in this lock through which the separated reaction water is removed (German Pat. No. 1,273,644 or U.S. Pat. No. 3,479,224).

An auxiliary gas under pressure, usually hydrogen which is taken from the fuel cell or the fuel cell battery is used for transporting the condensate from the gas chamber of the water separation cell to the lock. This auxiliary gas passes into the environment following the lock, which results in a large gas consumption. If hydrogen is used as the auxiliary gas, measures must be also taken to prevent the development of explosive hydrogen-air mixtures.

SUMMARY OF THE INVENTION

It is an object of the present invention to avoid, in a water separation cell of the type mentioned at the outset and comprising a liquid chamber and a gas chamber separated therefrom by a porous diaphragm, the disadvantages and dangers which are connected with discharging of the auxiliary gas into the environment and to ensure an economical transport of the condensate.

According to the present invention, this is achieved by subdividing the liquid chamber into two chambers of different size which are arranged on top of each other. The upper, larger chamber serves as the electrolyte chamber and the lower, smaller chamber takes up the condensate which passes through the porous diaphragm into this chamber due to the pressure of a gas present in the gas chamber.

In the device according to the present invention, gas losses no longer occur in connection with the transport of the condensate and the risks which result if hydrogen is discharged into the atomsphere are also eliminated. This device has the further advantage that the customary separate locks for removing the condensate can be dispensed with, since the appropriate devices are already integrated into the liquid chambers for the electrolyte which are provided anyhow. In the device according to the present invention, each gas or condensation chamber therefore has its own condensed water removal. The condensate, i.e., the condensed reaction water, is first transported into the associated chamber and is then removed from these chambers via a common manifold.

In comparison to the device known from the German Offenlegungsschrift No. 2,128,537 or the British patent Specification No. 1,396,157, in which a jet pump arranged in a gas supply line of the fuel cell battery serves for transporting the condensate, which generates a pressure difference between the gas chamber and the lock, and in which the auxiliary gas flowing along with the condensate from the gas chamber to the lock is returned to the jet pump, the device according to the present invention has, in particular, the advantage of a simple design and, connected therewith, a requirement for less material and labor in its construction. For, the lock and the jet pump with the associated lines, as well as the valves required therefor for adjusting the flow of auxiliary gas, are eliminated.

In the device according to the present invention, the area of the part of the diaphragm bounding the chamber for the condensate is advantageously about 5 to 20% and preferably, about 10% of the area of the part of the diaphragm bounding the electrolyte chamber. In this manner, it is ensured with certainty that enough reaction water can evaporate from the electrolytic liquid and it is also assured that the condensate developing in the gas chamber is transported completely into the chamber provided for this purpose, but not back into the electrolytic liquid. In comparison to the known water separation cell with a separate lock, the diaphragm area available for evaporation need be decreased, beyond this, only inappreciably, since in this device, a portion of the diaphragm cannot be used for evaporation anyhow to preclude the transport of the condensate back into the liquid chamber. In the water separation cell according to the present invention, the liquid chamber is advantageously enveloped by a frame and the electrolyte chamber is separated from the chamber for the condensate by a bar or crosspiece which is part of this frame. In this manner, the chambers for the condensate are fully integrated into the electrolyte frame and therefore require no additional parts in their construction. The electrolyte frames consist advantageously of plastic such as, for instance, polysulfone, and can be produced by injection molding. The bar between the two chambers, which may also be fastened in a suitable manner to the electrolyte frame, is advantageously curved in the direction toward the lower chamber, i.e., the chamber for the condensate. In this manner, a relatively high degree of position independence of the water separation cell according to the invention is obtained.

DETAILED DESCRIPTION OF THE INVENTION

Figure 1:
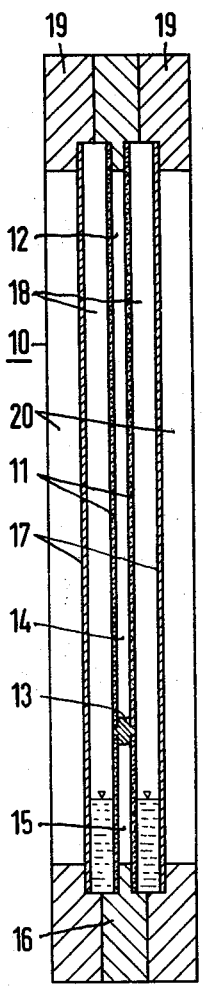
FIG. 1 is a crossection view of an embodiment of the present invention.

In the embodiment shown in FIG. 1, a water separation cell 10 according to the present invention having two porous diaphragms 11 is shown. These diaphragms, which consist of asbestos, enclose a liquid chamber 12. The liquid chamber 12 is subdivided by a bar 13 into an electrolyte chamber 14 and a chamber 15 for the condensed water. The bar 13 is part of the frame 16, which is called the electrolyte frame and holds the diaphragms 11. The diaphragms are cemented to part of the frame 16, as may be seen from FIG. 1. As may also be seen in FIG. 1, the diaphragms 11 are fastened to the bar 13 in a manner similar to that at the frame 16; for this purpose, the bar 13 has lateral projections. However, these projections may also be omitted (see FIG. 2), in which case the diaphragms then rest on the entire width of the bar and are cemented to the bar. In that case, it is advantageous to treat the diaphragms 11 hydrophobically in the region of the bar 13, in order to separate the electrolyte chamber 14 and the chamber 15 completely and to prevent the liquid to pass.

The diaphragms 11 and condensation surfaces 17 arranged at a distance therefrom form respective gas chambers 18. The condensation surfaces 17 consist, for instance, of plastic or of metal. On the back side of the condensation surfaces 17, which are arranged in a frame 19, cooling spaces 20 for receiving a coolant, particularly water, are provided. Air, for instance, can also be used as the cooling medium. The water, which evaporates through the diaphragms 11 from the electrolytic liquid flowing through the electrolyte chamber 12 is condensed at the cooling surfaces 17 and collects, as shown in FIG. 1, at the bottom, i.e., in the lower part of the gas chambers 18. Due to the pressure of the gas present therein, particularly hydrogen, the condensate is transported from the gas chambers 18 through the diaphragms 11 into the chamber 15 for the condensed water; the gas in the gas chamber may also be air, oxygen or nitrogen. From the chamber 15, the condensate gets into a manifold and is then discharged to the outside.

Figure 2:
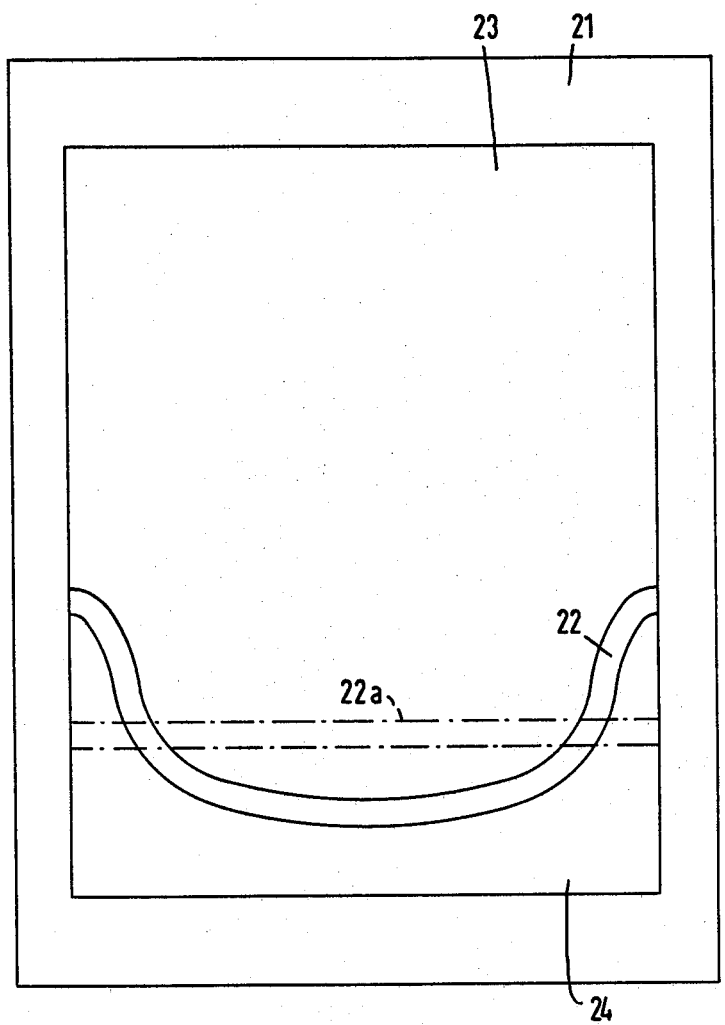
FIG. 2 is a view of an alternate form of electrolyte frame.

In FIG. 2, an alternate form of electrolyte frame for the water separation cell according to the present invention which is highly position independent is shown. The electrolyte frame 21 (corresponding to frame 16 of FIG. 1) which serves to accept the diaphragm, has a cross piece 22 (corresponding to 13 of FIG. 1) which is curved away from the electrolyte chamber 23 toward the chamber 24 for the condensed water. The two parts of the diaphragm which define the electrolyte chamber 23 and the chamber 24 for the condensed water, respectively, of course, then have a corresponding shape. The embodiment of FIG. 2, in which the cross piece 22 merges into the frame 21 at a relatively high level, has the following advantage: If the water separation cell is inclined to one side, there is hardly any danger that the condensate in the gas chamber will rise high enough at the frame 21 that it will reach the region above the cross piece 22 and could therefore pass through the diaphragm into the electrolyte chamber. The condensate level in the gas chamber will rather always be in the region below the cross piece and will therefore lie in the region of that part of the diaphragm which defines the chamber for the condensed water. In this manner, it is ensured that the effectiveness of the water separation cell is not affected adversely by lateral inclination.

With an arrangement of the cross piece as is indicated in FIG. 2 by the dash-dotted line, i.e., if a straight bar 22a is provided, on the other hand, it could more easily occur that, if the water separation cell is inclined, condensate will pass from the gas chamber into the electrolyte chamber, since the condensate in the gas chamber will reach the bar much sooner, i.e., it will reach the boundary between the part of the diaphragm in the region of the chamber for the condensed water and the part in the region of the electrolyte chamber much sooner.

What is claimed is:

1. In combination with a fuel cell or a fuel cell battery, an improved water separation cell for removing the reaction water from the electrolyte of the fuel cell or fuel cell battery comprising:
   a. a vertically extending liquid chamber bounded on at least one side by a porous diaphragm;
   b. a gas chamber vertically disposed adjacent said liquid chamber of essentially the same height as said liquid chamber bounded by said diaphragm on one side and by a condensation surface adapted for cooling; and
   c. means disposed essentially horizontally dividing said liquid chamber into two chambers of different size which are arranged one on top of the other, the upper chamber being larger than the lower chamber and serving as an electrolyte chamber and the lower smaller chamber acting to take up condensate which passes from said gas chamber through the porous diaphragm into said lower small chamber due to the pressure of a gas present in said gas chamber.

2. The improvement according to claim 1 wherein the area of the part of the diaphragm bounding the chamber for the condensate is about 5 to 20% of the area of the part bounding the electrolyte chamber.

3. The improvement according to claim 2 wherein said area is 10%.

4. The improvement according to claim 2 wherein said liquid chamber is enveloped by a frame and wherein the electrolyte chamber is separated from the chamber for the condensate by a bar which is part of said frame.

5. The improvement according to claim 4 wherein said frame is made of plastic.

6. The improvement according to claim 4 wherein said cross piece is curved in a direction toward the chamber for the condensate.

7. The improvement according to claim 1 wherein said liquid chamber is enveloped by a frame and wherein the electrolyte chamber is separated from the chamber for the condensate by a bar which is part of said frame.

8. The improvement according to claim 7 wherein said frame is made of plastic.

9. The improvement according to claim 7 wherein said cross piece is curved in a direction toward the chamber for the condensate.

* * * * *